(12) United States Patent
Lidman

(10) Patent No.: US 11,246,952 B2
(45) Date of Patent: Feb. 15, 2022

(54) ULTRAVIOLET SURFACE SANITIZING SYSTEM AND METHOD

(71) Applicant: David Lidman, Cotuit, MA (US)

(72) Inventor: David Lidman, Cotuit, MA (US)

(73) Assignee: STERILIT, LLC, Cotuit, MA (US)

( * ) Notice: Subject to any disclaimer, the term of this patent is extended or adjusted under 35 U.S.C. 154(b) by 0 days.

(21) Appl. No.: 16/824,386

(22) Filed: Mar. 19, 2020

(65) Prior Publication Data
US 2021/0290792 A1  Sep. 23, 2021

(51) Int. Cl.
*A61L 2/10* (2006.01)
*A61L 2/26* (2006.01)

(52) U.S. Cl.
CPC .............. *A61L 2/10* (2013.01); *A61L 2/26* (2013.01); *A61L 2202/11* (2013.01); *A61L 2202/14* (2013.01)

(58) Field of Classification Search
CPC ........................................................ A61L 2/10
See application file for complete search history.

(56) References Cited

U.S. PATENT DOCUMENTS

| | | | | |
|---|---|---|---|---|
| 6,610,990 B1* | 8/2003 | Moruzzi | ................... | A61L 2/10 |
| | | | | 210/198.1 |
| 8,277,741 B2* | 10/2012 | McCabe | ................ | H05B 47/16 |
| | | | | 422/186.3 |
| 2007/0071636 A1* | 3/2007 | Bovino | ..................... | A61L 2/10 |
| | | | | 422/24 |
| 2013/0279966 A1* | 10/2013 | Roberts | ..................... | A61L 2/10 |
| | | | | 401/207 |
| 2017/0333580 A1* | 11/2017 | Cahan | ........................ | A61L 2/24 |
| 2019/0170324 A1* | 6/2019 | Jones | ......................... | A61L 2/10 |
| 2020/0217102 A1* | 7/2020 | Gargash | ................... | A61L 2/10 |

* cited by examiner

*Primary Examiner* — Donald R Spamer
(74) *Attorney, Agent, or Firm* — Inspired Idea Solutions Law Firm

(57) ABSTRACT

A system and method for sanitizing a surface is disclosed. The surface is formed of a material transparent to ultraviolet light. Ultraviolet light is generated within the material opposite to the surface. The ultraviolet light passes through the material to illuminate and sanitize the surface. The material may be formed into the shape of a door handle which is sanitized. The system and method may also include a sensor for determining when to sanitize the surface.

17 Claims, 2 Drawing Sheets

ULTRAVIOLET SURFACE SANITIZING SYSTEM AND METHOD

BACKGROUND

Field

The disclosed systems and methods relate to systems which illuminate a surface with ultraviolet light to kill germs thereon.

Discussion of the Related Art

Diseases can be spread among people through contact with various surfaces. Germs and other biological matter can be deposited on surfaces when touched or items are placed thereon. Airborne germs may also land on surfaces. When others touch those surfaces, they can pick up the germs. Others may also pick up germs from items which have been placed on the surfaces. Therefore, a need exists for a mechanism for removing germs from a surface.

Germs can be removed from surfaces in various known ways. The most basic is washing the surface, which can remove the germs. Washing, however, may just move the germs around without removing them from the surface. Germs need specific environmental conditions to survive. Heat can kill germs. Thus, many surfaces are cleaned and sanitized with hot water or other heating means. The temperatures and time necessary to kill many germs is not conducive for its use on many surfaces.

Antibacterial cleaners contain chemicals which kill various germs. These cleaners can be applied using sprays or wipes. When cleaning a surface with an antibacterial cleaner, many of the remaining germs on a surface are killed. Use of antibacterial cleaners have become widespread, which has led to various other problems. Cleaner residue is deposited into the environment which may have detrimental effects on other living organisms. An increased prevalence of super bugs, i.e., germs which are not affected by cleaners, is believed to have resulted from overuse of cleaners. Therefore, a need exists for a sanitizing method which does not involve harmful chemicals.

Ultraviolet light or radiation is also known to kill germs. It has been used to purify water and other liquids. It can also be used to sanitize surfaces. U.S. Pat. No. 10,092,669 discloses a system for sanitizing a door handle after its use. The system includes a pair of ultraviolet light sources on either side of the handle. A sensor determines when the handle has been used and activates the lights. The effectiveness, however, of the ultraviolet radiation diminishes with distance to the surface. Therefore, the light sources have to be placed close to the handle. The light has to contact all parts of the surface. With shaped surfaces, illumination can be difficult due to shadowing. Thus, the positioning of the light sources can make use of the handle more difficult. Therefore, a need exists for a system which can sanitize a surface without interfering with its use.

SUMMARY

The disclosed systems and methods overcome deficiencies of the prior art in sanitizing a surface by forming the surface from a material which is transparent to ultraviolet radiation. An ultraviolet light source is positioned within the material. Ultraviolet radiation from the light source passes through the material to sanitize the surface.

DETAILED DESCRIPTION

Figure 1:
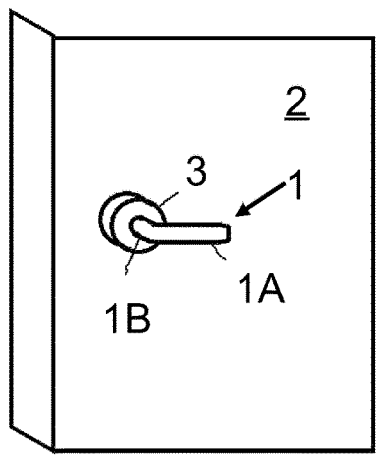
FIG. 1 is an illustration of a door handle according to an embodiment.

Features of the systems and methods are illustrated in the attached drawings. The drawings are merely representations of application of the disclosed systems and methods. FIG. 1 illustrates a door handle 1 according to an embodiment. The door handle 1 extends from a latching mechanism 3 which is in a door 2. As illustrated in FIG. 1, the door handle is formed like a rod with a bend forming a grasping part 1A and an offset part 1B. The offset part 1B positions the grasping part 1A away from the door so that it can be accessed by the hand to unlatch and open the door. The door handle 1 can rotate within the latching mechanism 3 as is known in the art to unlatch the door. According to an embodiment, at least an outer portion of the door handle is formed of a material which is transparent to ultraviolet light or radiation. Such material may include glass or plastic. The material should be sufficiently strong so as to function as a door handle while still passing the ultraviolet light.

Figure 2:
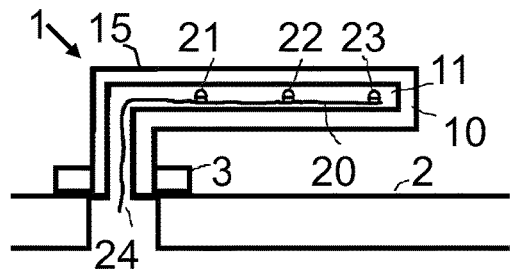
FIG. 2 is a cross-sectional view of the door handle of FIG. 1.

A cross-sectional view of an embodiment of the door handle 1 of FIG. 1 is illustrated in FIG. 2. As illustrated in FIG. 2, the door handle 1 consists of an outer part 10 formed of an ultraviolet light transparent material. A radiation system 20, consisting of one or more light emitting diodes (LEDs) 21, 22, 23 and electrical wiring 24 connecting the LEDs, is positioned within the outer part 10 of the handle 1. The electrical wiring 24 extends beyond the handle 1 into the interior of the door 2. The electrical wiring 24 is attached to a source of electrical power (not shown) within the door. The LEDs 21, 22, 23 are selected to emit ultraviolet light in a spectrum capable of killing germs. They may emit a broader spectrum of light, as long the appropriate ultraviolet spectrum is produced. Light from the LEDs 21, 22, 23 passes through the outer part 10 of the handle 1 resulting in sterilization of the outer surface 15 of the handle 1. The number and positioning of LEDs 21, 22, 23 within the handle 1 will depend upon the size and shape of the handle 1 and the intensity of the light from the LEDs 21, 22, 23. Refraction and reflection properties of the material from which the outer part 10 of the handle 1 is formed may also disperse the ultraviolet light so that the entire surface is properly irradiated.

FIG. 2 illustrates an empty space 11 within the outer part 10 of the handle 1 into which the radiation system 20 is positioned. Alternatively, the outer part 10 may form the entire handle with the radiation system 20 embedded within the outer part 10.

Figure 3:
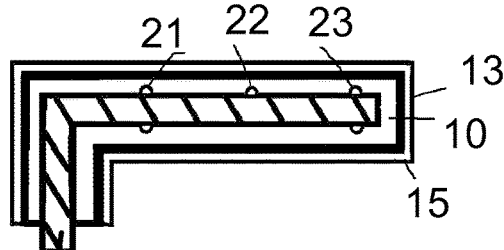
FIG. 3 is a cross-sectional view of a second embodiment of the door handle of FIG. 1.

FIG. 3 is a cross-sectional drawing illustrating a second embodiment of the handle 1. In this embodiment, a solid core 12 is positioned within the outer part 10. The solid core 12 may be of metal or other material so as to provide additional strength to the structure of the handle. As illustrated in FIG. 3, the LEDs 21, 22, 23 are embedded within the outer part 10 so that the solid core 12 fills the entire region within the outer part 10. A surface layer 13 may be included on an outer surface 15 of the outer part 10. The surface layer 13 may be a paint or other colorant to provide variation in the appearance of the outer part 10 of the handle 1. The surface layer 13 may be of a material and of a thickness such that the ultraviolet light can pass through it in order to sterilize the outer surface 15 of the surface layer.

Figure 4:
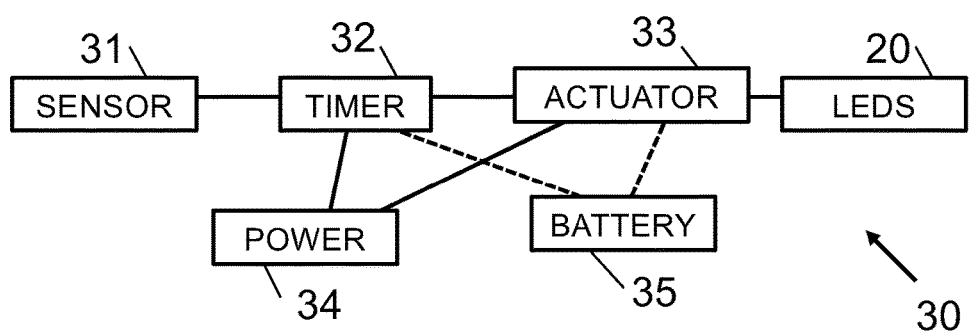
FIG. 4 is a block diagram of a first embodiment of a control system for the ultraviolet light source of the door handle of FIG. 1.

FIG. 4 is a block diagram 30 illustrating the operational components for the radiation system 20 according to an embodiment. As illustrated in FIG. 4, power source 34 from the building is provided through wiring in the door to an actuator 33 which illuminates the LEDs 21, 22, 23 of the radiation system 20. Alternatively, a battery 35 may provide the necessary power source. The battery 35 may be positioned within the door, the handle, or the latching mechanism. The battery 35 may be rechargeable. To control the timing of illumination, a sensor 31 is positioned relative to the handle 1 to determine when the handle has been touched or rotated. The sensor 31 may function to determine when the handle is used or when it is released. The sensor 31 is connected to a timer 32. The timer 32 controls operation of the actuator 33. If the sensor 31 determines when the handle is operated, the timer 32 may delay illumination of the LEDs 21, 22, 23 for an expected amount of time for operation of the handle so that the they are illuminated after it is released. Alternatively, the timer 32 may immediately illuminate the LEDs if the sensor 31 determines release of the handle 1. The timer 32 causes the LEDs 21, 22, 23 to be illuminated for sufficient time to properly sanitize the surface of the handle 1. The time may depend upon the shape of the handle and the thickness of the outer part 10. The time may also depend upon the environment in which the handle 1 is used. Some environments are more prone to germs and a longer illumination period may be appropriate. The sensor 31 may determine an action relating to the need to illuminate the handle 1, such as opening or closing of the door, motion through the doorway or near the door, etc.

Figure 5:
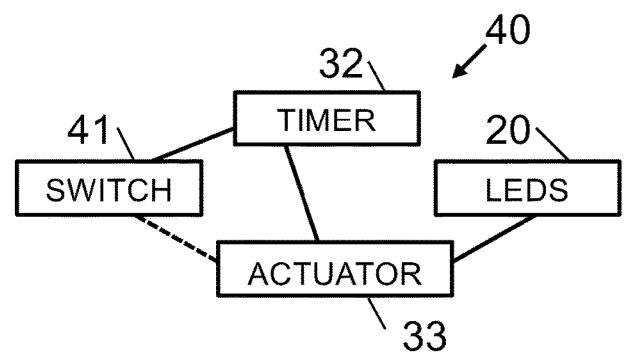
FIG. 5 is a block diagram of a second embodiment of a control system for the ultraviolet light source of the door handle of FIG. 1.

FIG. 5 illustrates another embodiment for operational components 40 for the radiation system 20. In this embodiment, a switch 41 is used to determine when to illuminate the LEDs 21, 22, 23. The switch 41 may start the timer 32 to control the illumination period. Alternatively, the switch 41 may be connected to the actuator 33 so that the switch 41 can be used to turn the illumination on and off.

Figure 6:
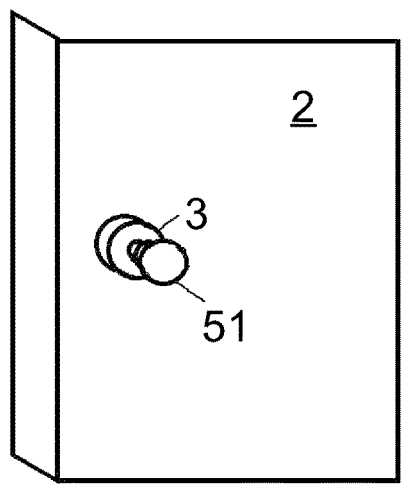
FIG. 6 is an illustration of a door handle according to a second embodiment.
Figure 7:
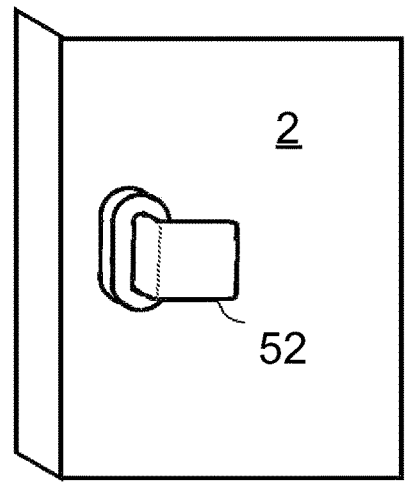
FIG. 7 is an illustration of a door handle according to a third embodiment.

FIGS. 1-3 illustrate a type of door handle 1 which extends from the door with a bend to allow it to be pushed up or down to operate the latching mechanism 3 for the door 2. Other types of door handles can also be used as FIGS. 1-3 only show one embodiment. FIG. 6 illustrates a doorknob 51 as is known in the art. The example doorknob 51 includes an outer part 10 which forms the knob. The radiation system 20 is positioned within the outer part 10 of the knob so as to provide illumination of the entire outer surface 15 of the knob. FIG. 7 illustrates another form of a door handle 52 as is known in the art. This door handle 52 is in the form a flat panel with a bend. This type of door handle is used in doors without a latching mechanism. The entire panel may form the outer part 10 of the handle 52. The radiation system 20 is positioned within the panel to provide illumination of front and back surfaces of the panel. The sensor 31 may measure pressure on the handle 52 to determine when it is used.

Figure 8:
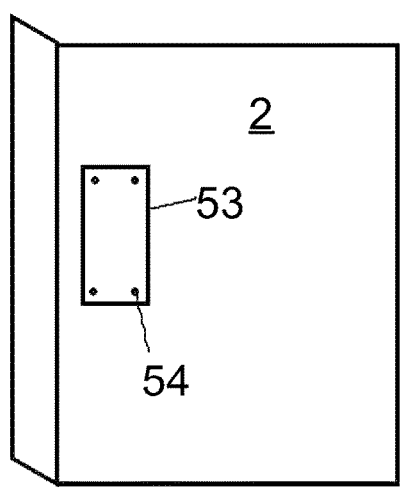
FIG. 8 is an illustration of a push panel for a door according to an embodiment.

FIG. 8 illustrates a door 2 without a handle which is opened by pushing. Sometimes, such a door includes material on the door where a person will typically push the door. The disclosed system can be used when pushing a door. A push panel 53 is attached to the door, typically with screws 54. The push panel may be on the surface of the door or may extend within the door. The top surface of the push panel 53 forms the outer part 10. The radiation system 20 is positioned behind the top surface of the push panel 53 and illuminates the top surface. The sensor 31 may measure pressure applied to the push panel 53.

Figure 9:
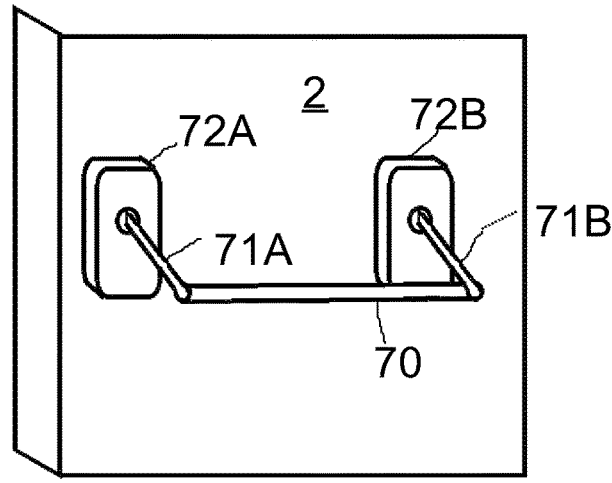
FIG. 9 is an illustration of a door release according to an embodiment.

FIG. 9 illustrates a door release structure known in the art. The release structure includes a bar 70 which the user pushes to unlatch the door 2. The bar 70 is attached to levers 71A, 71B at each end. The levers 71A, 71B extend from the latching mechanisms 72A, 72B for the door. The bar 70 includes the outer part 10 formed of an ultraviolet transparent material, substantially in the form of a cylinder. The radiation system 20 is retained within the bar 70 such that the surface of the cylinder of the bar 70 can be illuminated.

FIGS. 1-9 illustrate example systems related to door handles or push panels. The system, however, may also be used with other surfaces likely to contain germs. Other handles, such as faucet handles, toilet flush handles, appliance handles, and cabinet knobs, can be formed in accordance with the disclosed system having an outer part of an ultraviolet transparent material and a radiation system to provide ultraviolet illumination from inside the outer part to the surface of the outer part. Similarly, push buttons, such as elevator buttons, may have an outer surface 15 of ultraviolet transparent material with a radiation system being the surface. The push panel 53 illustrated in FIG. 8 could be used for any flat surface, such as counter tops. Also, other shapes could be formed, such as toilet seats. The rod shape of FIG. 9 could also be used on shopping cart and medical cart handles.

Having disclosed various embodiments, the present invention is not limited thereto except as set forth in the claims hereto.

The invention claimed is:

1. A surface sanitizing system comprising:
    a material substantially transparent to ultraviolet light formed in a shape such that at least a portion of the material forms the surface;
    a strengthening structure extending between opposing ends of the material opposite the portion of the material which forms the surface;
    a radiation system having a plurality of light emitting diodes for generating ultraviolet light positioned relative to the material opposite the portion of the material which forms the surface, the radiation system positioned between the surface and the strengthening structure; and
    means for operating the radiation system to illuminate the surface through the material so as to sanitize the surface.

2. The surface sanitizing system of claim 1, wherein the radiation system includes a power source.

3. The surface sanitizing system of claim 2, wherein the power source is a battery.

4. The surface sanitizing system of claim 1, wherein the means for operating includes a sensor for determining when the surface has been touched.

5. The surface sanitizing system of claim 1, wherein the material is formed in the shape of a door handle.

6. The surface sanitizing system of claim 1, wherein the material is formed in the shape of one of a flat panel and a push button.

7. The surface sanitizing system of claim 1, wherein the material is formed in the shape of a cylindrical rod.

8. A method of sanitizing a surface, the surface being formed by a material which is substantially transparent to ultraviolet light, a strengthening structure extending between opposing ends of the material opposite the portion of the material which forms the surface, the method comprising the steps of:

generating ultraviolet light from a radiation system having a plurality of light emitting diodes positioned relative to the material opposite the portion of the material which forms the surface, the radiation system positioned between the surface and the strengthening structure; and passing the ultraviolet light through the material to the surface.

9. The method of claim 8, further comprising the steps of:
determining when the surface has been touched, and
generating the ultraviolet light in response to the determining step.

10. The method of claim 8, further comprising the step of:
supporting the material when touched by means of the strengthening structure.

11. A surface sanitizing system comprising:
a material substantially transparent to ultraviolet light formed in a shape such that at least a portion of the material forms the surface;
a strengthening structure extending a length of the material opposite the portion of the material which forms the surface;
a radiation system having a plurality of light emitting diodes for generating ultraviolet light positioned relative to the material opposite the portion of the material which forms the surface, the radiation system positioned between the surface and the strengthening structure; and
means for operating the radiation system to illuminate the surface through the material so as to sanitize the surface.

12. The surface sanitizing system of claim 11, wherein the radiation system includes a power source.

13. The surface sanitizing system of claim 12, wherein the power source is a battery.

14. The surface sanitizing system of claim 11, wherein the means for operating includes a sensor for determining when the surface has been touched.

15. The surface sanitizing system of claim 11, wherein the material is formed in the shape of a door handle.

16. The surface sanitizing system of claim 11, wherein the material is formed in the shape of a flat panel.

17. The surface sanitizing system of claim 11, wherein the material is formed in the shape of a cylindrical rod.

\* \* \* \* \*